(12) United States Patent
Marescaux et al.

(10) Patent No.: US 9,596,980 B2
(45) Date of Patent: Mar. 21, 2017

(54) ENDOSCOPE SYSTEM WITH PIVOTABLE ARMS

(75) Inventors: Jacques Francois Bernard Marescaux, Scharrachbergheim (FR); Jeffrey S. Melanson, Sturbridge, MA (US); Bernard Dallemagne, Beauafys (BE); Joel Leroy, Schiltigheim (FR); Didier Mutter, Vendenheim (FR); James P. Barry, Charlton, MA (US); Stefan Storz, Wurmlingen (DE); Martin Leonhard, Emmingen (DE)

(73) Assignee: Karl Storz Endovision, Inc., Charlton, MA (US)

( * ) Notice: Subject to any disclaimer, the term of this patent is extended or adjusted under 35 U.S.C. 154(b) by 1466 days.

(21) Appl. No.: 11/739,833

(22) Filed: Apr. 25, 2007

(65) Prior Publication Data

US 2008/0269562 A1 Oct. 30, 2008

(51) Int. Cl.
*A61B 1/00* (2006.01)
*A61B 1/04* (2006.01)
(Continued)

(52) U.S. Cl.
CPC .......... *A61B 1/018* (2013.01); *A61B 1/00087* (2013.01); *A61B 1/00098* (2013.01);
(Continued)

(58) Field of Classification Search
USPC ............... 600/104, 106, 107, 114, 101, 115, 600/121–125, 127–129, 139–142,
(Continued)

(56) References Cited

U.S. PATENT DOCUMENTS 3,667,474 A 6/1972 Lapkin et al.
3,896,793 A 7/1975 Mitsui et al. ..................... 128/6
(Continued)

FOREIGN PATENT DOCUMENTS

JP 2001212078 A 8/2001
WO 2005044095 A1 5/2005
(Continued)

OTHER PUBLICATIONS

European Search Report & Written Opinion; EP 08 00 7936; Sep. 3, 2009; 7 pages.
(Continued)

*Primary Examiner* — Ryan Henderson
(74) *Attorney, Agent, or Firm* — Whitmyer IP Group LLC

(57) ABSTRACT

An endoscopic surgery apparatus is provided, including a tubular member, a handle located on a proximal end of the tubular member, and one or more pivotable arms detachably connected to a distal end of the tubular member. The tubular member has channels along its longitudinal axis, wherein at least one of the channels is an optical channel and at least one other channel is an illumination channel. The arms have guiding channels adapted to receive surgical tools, which direct the surgical tools. The arms are interchangeable with other arms of different configurations. Also, said arms have an open and a closed position, such that when the arms are in the closed position an opening is defined allowing viewing of a surgical site via the optical channel.

18 Claims, 6 Drawing Sheets

(51) Int. Cl.
*A61M 5/178* (2006.01)
*A61B 1/32* (2006.01)
*A61B 1/018* (2006.01)
*A61B 17/02* (2006.01)
*A61B 17/29* (2006.01)
*A61B 17/34* (2006.01)

(52) U.S. Cl.
CPC .. *A61B 17/0218* (2013.01); *A61B 2017/2906* (2013.01); *A61B 2017/3445* (2013.01); *A61B 2017/3447* (2013.01)

(58) Field of Classification Search
USPC ........ 600/146–153, 160–182, 204, 219–225; 606/1, 167, 170, 183, 185, 190, 191, 198, 606/200–205; 604/44, 104–109
See application file for complete search history.

(56) References Cited

U.S. PATENT DOCUMENTS

| | | | |
|---|---|---|---|
| 3,915,157 A | 10/1975 | Mitsui | 128/6 |
| 3,924,608 A | 12/1975 | Mitsui | 128/2 |
| 4,436,087 A | 3/1984 | Ouchi | 128/6 |
| 4,653,476 A | 3/1987 | Bonnet | 128/4 |
| 4,949,706 A | 8/1990 | Thon | 128/4 |
| 5,025,778 A | 6/1991 | Silverstein et al. | 128/4 |
| 5,037,433 A | 8/1991 | Wilk et al. | 606/139 |
| 5,259,366 A | 11/1993 | Reydel et al. | 128/4 |
| 5,312,391 A | 5/1994 | Wilk | |
| 5,353,784 A | 10/1994 | Nady-Mohamed | |
| 5,386,818 A | 2/1995 | Schneebaum et al. | 128/4 |
| 5,474,057 A | 12/1995 | Makower et al. | |
| 5,483,951 A | 1/1996 | Frassica et al. | 600/104 |
| 5,503,616 A | 4/1996 | Jones | 600/155 |
| 5,549,637 A * | 8/1996 | Crainich | 606/207 |
| 5,569,164 A | 10/1996 | Lurz | 600/158 |
| 5,624,398 A | 4/1997 | Smith et al. | |
| 5,630,782 A | 5/1997 | Adair | 600/133 |
| 5,667,473 A * | 9/1997 | Finn et al. | 600/104 |
| 5,674,181 A * | 10/1997 | Iida | 600/127 |
| 5,749,889 A | 5/1998 | Bacich et al. | 606/198 |
| 5,820,546 A | 10/1998 | Ouchi | 600/123 |
| 5,827,177 A | 10/1998 | Oneda et al. | 600/121 |
| 5,833,656 A | 11/1998 | Smith et al. | |
| 5,885,207 A | 3/1999 | Iwasaka | 600/139 |
| 5,904,647 A * | 5/1999 | Ouchi | 600/104 |
| 5,921,915 A | 7/1999 | Aznoian et al. | 600/104 |
| 5,954,692 A | 9/1999 | Smith et al. | |
| 5,993,461 A | 11/1999 | Abae | |
| 5,995,875 A | 11/1999 | Blewett et al. | 607/98 |
| 6,059,719 A | 5/2000 | Yamamoto et al. | |
| 6,066,090 A | 5/2000 | Yoon | 600/113 |
| 6,071,233 A | 6/2000 | Ishikawa et al. | 600/104 |
| 6,106,521 A | 8/2000 | Blewett et al. | 606/41 |
| 6,179,776 B1 | 1/2001 | Adams et al. | 600/121 |
| 6,296,635 B1 | 10/2001 | Smith et al. | |
| 6,352,503 B1 | 3/2002 | Matsui et al. | 600/104 |
| 6,409,727 B1 | 6/2002 | Bales et al. | 606/47 |
| 6,458,074 B1 | 10/2002 | Matsui et al. | |
| 6,497,651 B1 | 12/2002 | Kan et al. | |
| 6,524,398 B2 | 2/2003 | Arora et al. | |
| 7,029,435 B2 | 4/2006 | Nakao | 600/153 |
| 7,060,024 B2 | 6/2006 | Long et al. | 600/106 |
| 2002/0058961 A1* | 5/2002 | Aguilar et al. | 606/198 |
| 2003/0040657 A1* | 2/2003 | Yamaya | A61B 1/00039 600/107 |
| 2003/0130674 A1 | 7/2003 | Kasahara et al. | |
| 2004/0077999 A1 | 4/2004 | Selmon et al. | |
| 2004/0111009 A1* | 6/2004 | Adams et al. | 600/114 |
| 2004/0220595 A1* | 11/2004 | Frazier et al. | 606/151 |
| 2005/0096502 A1* | 5/2005 | Khalili | 600/106 |
| 2005/0107664 A1 | 5/2005 | Kalloo et al. | |
| 2005/0113640 A1* | 5/2005 | Saadat et al. | 600/106 |
| 2005/0154386 A1* | 7/2005 | West et al. | 606/41 |
| 2005/0234294 A1* | 10/2005 | Saadat et al. | 600/104 |
| 2005/0234297 A1* | 10/2005 | Devierre et al. | 600/153 |
| 2006/0189845 A1 | 8/2006 | Maahs et al. | |
| 2007/0135686 A1* | 6/2007 | Pruitt et al. | 600/214 |
| 2007/0167679 A1* | 7/2007 | Miyamoto et al. | 600/106 |
| 2007/0167680 A1* | 7/2007 | Miyamoto et al. | 600/106 |
| 2007/0260273 A1 | 11/2007 | Cropper et al. | |
| 2008/0243031 A1* | 10/2008 | Seibel et al. | 600/566 |
| 2010/0036198 A1 | 2/2010 | Tacchino et al. | |

FOREIGN PATENT DOCUMENTS

| | | |
|---|---|---|
| WO | 2005104927 A2 | 11/2005 |
| WO | 2006046263 A1 | 5/2006 |
| WO | 2006110275 A2 | 10/2006 |
| WO | WO 2007/080974 | 7/2007 |
| WO | 2007104397 A1 | 9/2007 |

OTHER PUBLICATIONS

European Search Report Application No. EP 14 17 1731 Completed: Sep. 22, 2014; Mailing Date: Sep. 30, 2014 6 pages.

\* cited by examiner

ENDOSCOPE SYSTEM WITH PIVOTABLE ARMS

FIELD OF THE INVENTION

The present invention relates to an apparatus for endoscopic surgery and more specifically to an apparatus for transgastric or transluminal endoscopic surgery.

BACKGROUND OF THE INVENTION

The traditional method of abdominal surgery involves creating an incision in a patient large enough so that the surgeon can work with and handle directly the patient's organs and tissues. Unfortunately, this traditional method carries with it a relatively high risk of infection due to the exceptional amount of exposure to which the patient's internal organs are subjected during the surgery. Other significant drawbacks associated with traditional methods of abdominal surgery are the length of recovery time required for a patient and the significant pain suffered because of the size of the incision.

These negative effects of surgical treatment were significantly mitigated by the introduction of endoscopic surgery. Endoscopic surgery generally involves making one or more relatively small incisions in a patient's abdomen and then inserting one or more small surgical tools. The surgical tools are generally mounted on one end of a long, thin element having on the other end a handle and a means for actuating or manipulating the surgical tool. The endoscopic surgical tools are also often outfitted with optical and light-delivery channels so that the surgeon can view the area of the surgery.

While the advent of endoscopic surgical techniques significantly reduced the drawbacks of traditional surgical techniques, endoscopic surgery still involves a relatively high risk of infection, a relatively long recovery period, and significant pain for the patient. Recently, these negative effects have been even further reduced by the introduction of transgastric and transluminal endoscopic surgery.

In transgastric surgery, for example, an endoscopic tool is inserted into the patient's mouth and fed to the patient's stomach. The wall of the patient's stomach can then be punctured so that the tool can access other parts of the patient's abdomen. An incision in the wall of the stomach is preferable to external incisions because there are no nerve endings in the stomach. Transgastric endoscopic surgery reduces patient pain and recovery time as well as the risk of infection.

The endoscopic tool that is inserted into the patient for transgastric or transluminal surgery generally includes one or more surgical tools, an optical channel, one or more light channels, and/or one or more channels for evacuation or insufflation. The tools preferably have other unique features. First, they preferably are designed such that insertion into the patient's body is easy and causes the patient a minimum of trauma. Second, the tool preferably provides a means for multiple surgical tools to be used to exert force or perform functions in multiple directions at the surgical site. This is more difficult in transgastric and transluminal surgery because there is only one possible angle of approach since the tools are preferably inserted in the same place, for example, the patient's mouth. In conventional endoscopic surgery on the other hand, tools can be inserted at multiple locations so that the surgeon has an advantageous 'working triangle.' The working triangle allows the surgeon to exert force in multiple directions and therefore better perform surgical tasks. In transgastric and transluminal surgery, it is more difficult to create this working triangle since the tools are inserted parallel to one another.

There are various examples in the prior art of endoscopic tools which are intended for or could be used in transgastric or transluminal surgery and which attempt to address the foregoing concerns. For example, U.S. Pat. No. 6,066,090 to Yoon, U.S. Pat. No. 6,352,503 to Matsui et al., and U.S. Pat. No. 7,029,435 to Nakao all disclose endoscopic surgical apparatuses.

Yoon discloses an endoscope with two or more flexible branches, which are independently steerable, and include a source of illumination, a means for viewing the surgical site, and an operating channel through which surgical instruments may be passed. The two branches may be used to approach a surgical site from two angles so that the surgeon has two distinct views of the site and two angles in which force can be exerted.

The device disclosed by Yoon, however, suffers from significant drawbacks. Among the most notable of these is the fact that each branch of the endoscope must be separately steered and manipulated in order to obtain the proper positioning of the system at the surgical site. This increases the difficulty and hence duration of a surgery.

Matsui et al. discloses an endoscope and two treating tools which are inserted into a body cavity of a patient. The distance between the treating tools is adjusted by a distance adjusting device such as a balloon or an expandable basket.

The apparatus disclosed by Matsui et al. has significant drawbacks, however. Most significant of these drawbacks is its complexity. As shown in FIGS. 1 and 7 it contemplates insertion of an outer tube unit for guiding at least the insertion of an endoscope, two "treating tool leading insertion tools," and two treating tools. The method of creating distance between the treating tools, either by means of a balloon or expandable basket, further increases the complexity of the system because the distance adjusting device requires manual engagement.

Nakao discloses a flexible fiber optic endoscope which is split longitudinally on its distal end into working segments. The split allows a plurality of working elements which extend through working channels of the working segments to be separated from one another and independently maneuvered. During insertion, a sheath is used to temporarily join the working segments.

While the design of Nakao appears to provide a relatively simple solution to the above-described problems, it also has notable limitations. First, operation of the system is unduly complex as a result of the various components which must be manipulated in order to begin surgery. The sheath must be moved in order to allow the segments to separate. Each working segment must be positioned, the visualization segment must be positioned, and then the surgical tools must be manipulated. This is a complex process that would most likely require many individuals. Second, while the longitudinal split may allow for suitable separation of the working segments and thus the working elements, it is unclear from the figures or the description that there is adequate provision for redirecting the working elements back toward the longitudinal axis where the surgical site is located to form the working triangle.

Therefore, what is needed is an endoscopic surgery apparatus that has a thin profile so that it is easy to insert into the patient and that provides the surgeon with the ability to exert force in multiple directions at the surgical site.

SUMMARY OF THE INVENTION

Accordingly, it is an object of the present invention to provide an endoscopic surgical system which minimizes the risk of infection, the recovery time, and the pain associated with surgery. More specifically, it is an object of the present invention to provide a system for transgastric endoscopic surgery.

It is a further object of the present invention to provide a system for transgastric or transluminal endoscopic surgery which has a thin profile so as to be easily insertable into a patient.

It is a another object of the present invention to provide a system for transgastric or transluminal endoscopic surgery with a thin profile that is capable of creating an effective working triangle for the surgeon.

It is yet a further object of the present invention to provide a system for transgastric or transluminal endoscopic surgery which allows easy illumination and viewing of a surgical site.

It is yet another object of the present invention to provide a system for transgastric or transluminal endoscopic surgery wherein fluid matter may be easily delivered to a surgical site.

These and other objects are accomplished in accordance with one embodiment of the present invention by an endoscopic surgery apparatus, which includes a tubular member having a plurality of channels along its longitudinal axis, a handle located on a proximal end of the tubular member, and two or more arms pivotably connected to a distal end of the tubular member by hinges. The arms have guiding channels passing therethrough adapted to receive endoscopic surgical tools.

In some embodiments, the distal end of the tubular member articulates. In some embodiments, the tubular member includes a shaft portion coupled to the handle, a series of vertebrae coupled to the shaft portion, and a head member coupled to the most distal vertebra of the series of vertebrae. In some other embodiments, the head member is the distal end to which the arms are pivotably connected. In some embodiments, the head member is detachable from the series of vertebrae and replaceable with a head member of a different configuration. In some embodiments, the vertebrae are moveable relative to one another via a control on the handle such that the distal end of the tubular member articulates.

In other embodiments, the handle includes a mechanism for pivoting the arms between a closed position and open positions and the mechanism permits locking the arms in any selected position. In some other embodiments, the arms are adapted to grasp tissue at a surgical site when the arms are pivoted. In some embodiments, the arms include a blade portion adapted to cut tissue when the arms are pivoted. In some other embodiments, the arms are adapted to displace tissue when the arms are pivoted. In some embodiments, the arms are detachably connected to the distal end of the tubular member and are interchangeable with arms of different configurations.

In some other embodiments, one of the channels is an optical channel for the transmission of images and at least one other of the channels is an illumination channel for the transmission of light. In some other embodiments, the arms have a closed position and when the arms are in the closed position an opening is defined for viewing of a surgical site via the optical channel and illumination of a surgical site via the at least one illumination channel. In some other embodiments, when the arms are in the closed position they form an obturator shape adapted to temporarily displace tissue during insertion of the endoscopic surgery apparatus into a body.

In some other embodiments, the tubular member includes at least one working channel adapted to receive an endoscopic surgical tool. In some other embodiments, the arms may include deflecting members formed thereon for deflecting the endoscopic surgical tool running through the working channel.

In some other embodiments, the tubular member is formed of a flexible, plastic material. In some other embodiments, the handle includes controls for controlling a camera utilizing the optical channel to view a surgical site. In some other embodiments, at least one channel is adapted to deliver fluid or gas matter to a surgical site. In some other embodiments, at least one channel is adapted to remove fluid, gas, or solid matter from a surgical site. In some other embodiments, the distal end of the tubular member is electrically isolated from the proximal end of the tubular member. In some other embodiments, the ambient pressure at the distal end of the tubular member may be monitored via one of the channels along the longitudinal axis of the tubular member.

According to another embodiment of the present invention, an endoscopic surgery apparatus is provided, which includes a tubular member having a plurality of channels along its longitudinal axis, a handle located on a proximal end of the tubular member; and two or more surgical tool guide members detachably connected to a distal end of the tubular member and have guiding channels passing therethrough adapted to receive endoscopic surgical tools. The surgical tool guide members are interchangeable with other surgical tool guide members of different configurations.

In some embodiments, the distal end of the tubular member articulates. In some other embodiments, the tubular member comprises a shaft portion coupled to the handle, a series of vertebrae coupled to the shaft portion, and a head member coupled to the most distal vertebra of the series of vertebrae. The head member is the distal end to which the arms are pivotably connected. In some embodiments, the head member is detachable from the series of vertebrae and replaceable with a head member of a different configuration. In some embodiments, the vertebrae are moveable relative to one another via a control on the handle such that the distal end of the tubular member articulates.

In some embodiments, the surgical tool guide members are pivotably connected to the distal end of the tubular member. In some other embodiments, the handle includes a mechanism for pivoting the surgical tool guide members between a closed position and open positions. In other embodiments, the mechanism locks the surgical tool guide members in any selected position. In some other embodiments, the surgical tool guide members are adapted to grasp tissue at a surgical site when the surgical tool guide members are pivoted. In some embodiments, the surgical tool guide members include a blade portion adapted to cut tissue when the surgical tool guide members are pivoted. In some other embodiments, the surgical tool guide members are adapted to displace tissue when the surgical tool guide members are pivoted.

In some embodiments, one of the channels is an optical channel for the transmission of images and at least one other of the channels is an illumination channel for the transmission of light. In some other embodiments, the surgical tool guide members have a closed position, and when the surgical tool guide members are in the closed position an opening is defined allowing for viewing of a surgical site via the optical channel and illumination of a surgical site via the at least one illumination channel. In some other embodiments, when the surgical tool guide members are in the closed position they form an obturator shape adapted to temporarily displace tissue during insertion of the endoscopic surgery apparatus into a body.

In some other embodiments, at least one of the plurality of channels is adapted to receive an endoscopic surgical tool. In some embodiments, the surgical tool guide members may include deflecting members formed thereon for deflecting the endoscopic surgical tool.

In some embodiments, the tubular member is formed of a flexible, plastic material. In some other embodiments, the handle includes controls for controlling a camera utilizing the optical channel to view a surgical site. In some other embodiments, at least one channel is adapted to deliver fluid or gas matter to a surgical site. In some other embodiments, at least one channel is adapted to remove fluid, gas, or solid matter from a surgical site. In some other embodiments, the distal end of the tubular member is electrically isolated from the proximal end of the tubular member. In some other embodiments, the ambient pressure at the distal end of the tubular member may be monitored via one of the channels along the longitudinal axis of the tubular member.

According to yet another embodiment of the present invention, an endoscopic surgery apparatus is provided, which includes a tubular member having a plurality of channels along its longitudinal axis, and at least one of the channels of the tubular member is an optical channel for the transmission of images and at least one other of the channels is an illumination channel for the transmission of light. The apparatus also includes a handle located on a proximal end of the tubular member and two or more arms pivotably connected to a distal end of the tubular member. The arms have a closed position, and when the arms are in the closed position an opening is defined allowing for viewing a surgical site via the optical channel and illumination of a surgical site via the at least one illumination channel.

In some embodiments, the distal end of the tubular member articulates. In some other embodiments, the tubular member comprises a shaft portion coupled to the handle, a series of vertebrae coupled to the shaft portion, and a head member coupled to the most distal vertebra of the series of vertebrae. The head member is the distal end to which the arms are pivotably connected. In some embodiments, the head member is detachable from the series of vertebrae and replaceable with a head member of a different configuration. In some embodiments, the vertebrae are moveable relative to one another via a control on the handle such that the distal end of the tubular member is articulable.

In some embodiments, the arms have guiding channels passing therethrough to receive endoscopic surgical tools. In some other embodiments, the arms are detachably connected to the distal end of the tubular member and are interchangeable with other arms of a different configuration.

In some embodiments, at least one of the plurality of channels is a working channel adapted to receive an endoscopic surgical tool. In some other embodiments, the arms may have deflecting members formed thereon for deflecting an endoscopic surgical tool that is inserted into the working channel. In some other embodiments, the tubular member is formed of a flexible, plastic material.

In some embodiments, the handle includes a mechanism for pivoting the arms between a closed position and open positions. In some other embodiments, the mechanism permits locking the arms in any selected position. In some other embodiments, the arms are adapted to grasp tissue at a surgical site when the arms are pivoted. In some other embodiments, the arms include a blade portion adapted to cut tissue when the arms are pivoted. In some other embodiments, the arms are adapted to displace tissue when the arms are pivoted. In some embodiments, the handle includes controls for controlling a camera utilizing the optical channel to view a surgical site.

In some other embodiments, at least one channel is adapted to deliver fluid or gas matter to a surgical site. In some other embodiments, at least one channel is adapted to remove fluid, gas, or solid matter from a surgical site. In some other embodiments, the distal end of the tubular member is electrically isolated from the proximal end of the tubular member. In some other embodiments, the ambient pressure at the distal end of the tubular member may be monitored via one of the channels along the longitudinal axis of the tubular member.

According to still another embodiment of the present invention, an endoscopic surgery apparatus is provided, which includes a tubular member having a plurality of channels along its longitudinal axis, a handle located on a proximal end of the tubular member, and two or more surgical tool guide members connected to a distal end of the tubular member. At least one of the plurality of channels is a working channel adapted to receive an endoscopic surgical tool and the surgical tool guide members may have deflecting members formed thereon for deflecting the endoscopic surgical tool.

In some embodiments, the distal end of the tubular member articulates. In some other embodiments, the tubular member comprises a shaft portion coupled to the handle, a series of vertebrae coupled to the shaft portion, and a head member coupled to the most distal vertebra of the series of vertebrae. The head member is the distal end to which the arms are pivotably connected. In some embodiments, the head member is detachable from the series of vertebrae and replaceable with a head member of a different configuration. In some other embodiments, the vertebrae are moveable relative to one another via a control on the handle such that the distal end of the tubular member articulates.

In some embodiments, the surgical tool guide members are pivotably connected to the distal end of the tubular member and have guiding channels passing therethrough adapted to receive endoscopic surgical tools. In some other embodiments, the handle includes a mechanism for pivoting the surgical tool guide members between a closed position and open positions. In some other embodiments, the mechanism locks the surgical tool guide members in any selected position. In some embodiments, the surgical tool guide members are adapted to grasp tissue at a surgical site when the surgical tool guide members are pivoted. In some other embodiments, the surgical tool guide members include a blade portion adapted to cut tissue when the surgical tool guide members are pivoted. In some other embodiments, the surgical tool guide members are adapted to displace tissue when the surgical tool guide members are pivoted. In some other embodiments, the surgical tool guide members are detachably connected to the distal end of the tubular member and are interchangeable with other surgical tool guide members having different configurations.

In some embodiments, one of the channels is an optical channel for the transmission of images and at least one other of the channels is an illumination channel for the transmission of light. In some other embodiments, the surgical tool guide members have a closed position, when the surgical tool guide members are in the closed position and opening is defined for viewing of a surgical site via the optical channel and illumination of a surgical site via the at least one illumination channel. In some other embodiments, when the surgical tool guide members are in the closed position they form an obturator shape adapted to temporarily displace tissue during insertion of the endoscopic surgery apparatus into a body.

In some embodiments, the tubular member is formed of a flexible, plastic material. In some other embodiments, the handle includes controls for controlling a camera utilizing the optical channel to view a surgical site. In some other embodiments, at least one channel is adapted to deliver fluid or gas matter to a surgical site. In some other embodiments, at least one channel is adapted to remove fluid, gas, or solid matter from a surgical site. In some other embodiments, the distal end of the tubular member is electrically isolated from the proximal end of the tubular member. In some other embodiments, the ambient pressure at the distal end of the tubular member may be monitored via one of the channels along the longitudinal axis of the tubular member.

According to yet another embodiment of the present invention, an endoscopic surgery apparatus is provided, which includes a tubular member, a handle located on a proximal end of the tubular member, and one or more pivotable arms detachably connected to a distal end of the tubular member. The tubular member has a plurality of channels along its longitudinal axis, and at least one of the channels is an optical channel for transmission of images, at least one other channel is an illumination channel for the transmission of light, and at least one other channel is a working channel adapted to receive endoscopic surgical tools. The one or more pivotable arms have guiding channels passing therethrough adapted to receive surgical tools, and the arms may have deflecting members formed thereon for deflecting the endoscopic surgical tool emerging from the working channel. The arms are interchangeable with other arms of different configurations and the arms have a closed position, such that when the arms are in the closed position an opening is defined allowing viewing of a surgical site via the optical channel and illumination of a surgical site via the illumination channel.

In some embodiments, the distal end of the tubular member articulates. In some other embodiments, the tubular member comprises a shaft portion coupled to the handle, a series of vertebrae coupled to the shaft portion, and a head member coupled to the most distal vertebra of the series of vertebrae. The head member is the distal end to which the arms are pivotably connected. In some embodiments, the head member is detachable from the series of vertebrae and replaceable with a head member of a different configuration. In some embodiments, the vertebrae are moveable relative to one another via a control on the handle such that the distal end of the tubular member articulates.

In some other embodiments, the tubular member is formed of a flexible, plastic material. In some embodiments, the handle includes a mechanism for pivoting the arms between a closed position and open positions. In some other embodiments, the mechanism locks the arms in any selected position. In some other embodiments, the arms are adapted to grasp tissue at a surgical site when the arms are pivoted. In some embodiments, the arms include a blade portion adapted to cut tissue when the arms are pivoted. In some other embodiments, the arms are adapted to displace tissue when the arms are pivoted.

In some other embodiments, the handle includes controls for controlling a camera utilizing the optical channel to view a surgical site. In some other embodiments, at least one channel is adapted to deliver fluid or gas matter to a surgical site. In some other embodiments, at least one channel is adapted to remove fluid, gas, or solid matter from a surgical site. In some other embodiments, the distal end of the tubular member is electrically isolated from the proximal end of the tubular member. In some other embodiments, the ambient pressure at the distal end of the tubular member may be monitored via one of the channels along the longitudinal axis of the tubular member.

DETAILED DESCRIPTION OF AN EMBODIMENT OF THE INVENTION

Figure 1:
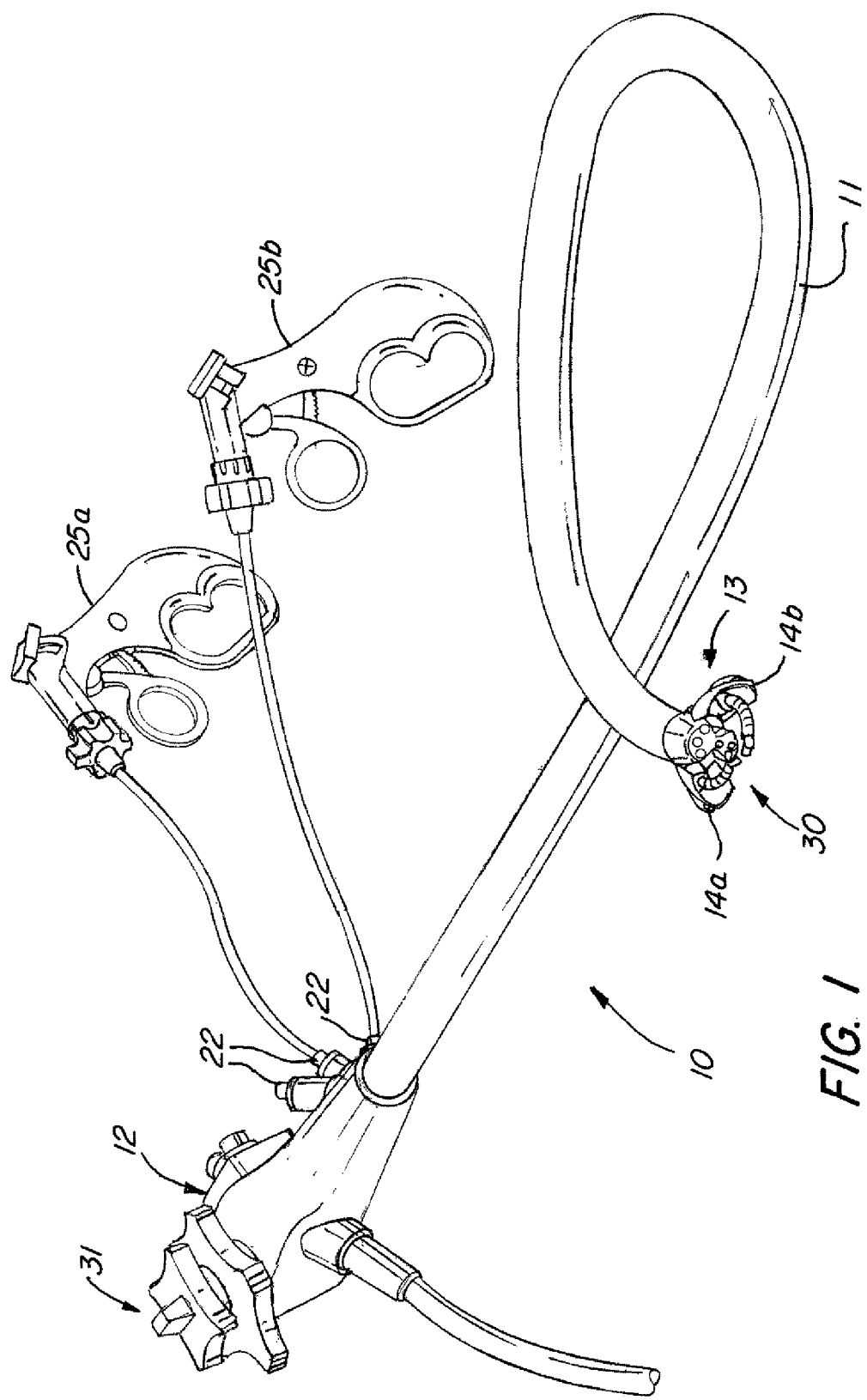
FIG. 1 is a perspective view of an endoscopic surgery apparatus according to one embodiment of the present invention.

Referring now to FIG. 1, an endoscopic surgery apparatus 10 is shown according to one embodiment of the present invention. Endoscopic surgery apparatus 10 includes tubular member 11 and handle 12 which is located on a proximal end 31 of tubular member 11. At the distal end 30 of tubular member 11 is a head portion 13 of the apparatus 10, having two pivotable arms 14a and 14b fixed thereon. Two surgical tools 25a and 25b are also shown in FIG. 1. The surgical tools 25a and 25b are shown inserted into the endoscopic surgery apparatus 10 at proximal terminals 22 of working channels running along the longitudinal axis of the tubular member 11.

The term "tubular member" as used throughout this application refers to many possible configurations. In one embodiment, the tubular member 11 has a shaft at its proximal end that is attached to the handle 12 and is substantially inflexible. Attached to the shaft portion is a series of articulating vertebrae, the articulation of which is controlled by the surgeon using control mechanisms on the handle. In that embodiment, the head portion 13 is either the last vertebra of the series of vertebrae or a special member attached to the last vertebra. In another embodiment, the tubular member 11 could be a single element, constructed out of a flexible material designed to have a selected degree of plasticity and elasticity. In that embodiment, the head portion 13 may or may not be a separate element distinct from the tubular member 11, but merely the most distal portion of the tubular member 11.

Figure 2:
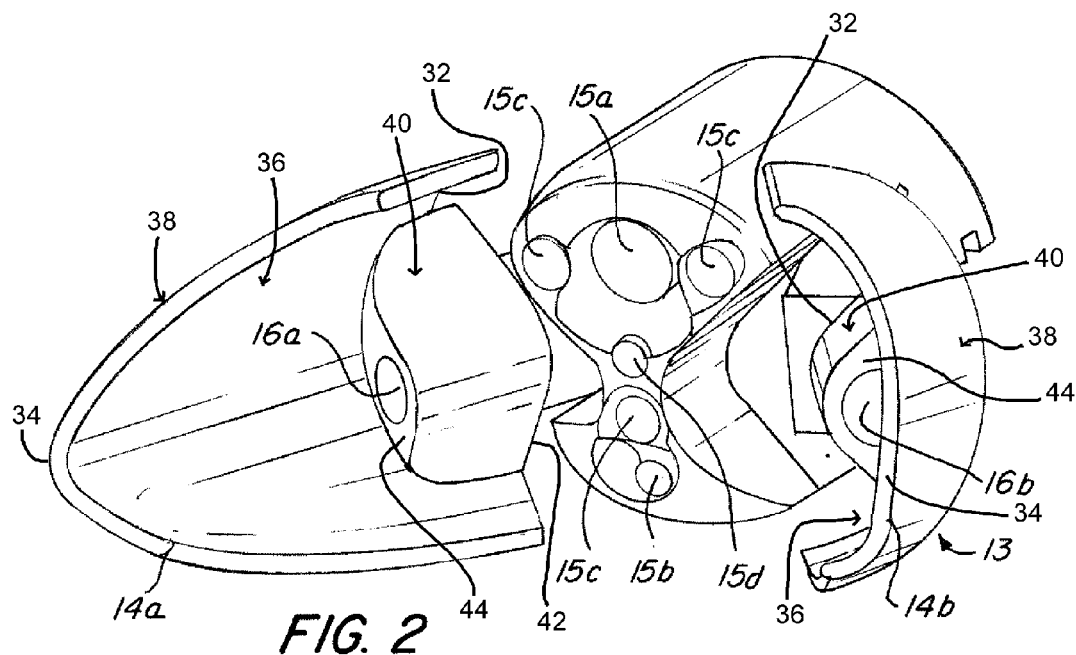
FIG. 2 is a perspective view of the distal end of the endoscopic surgery apparatus of FIG. 1, with arms in an open position.

FIG. 2 shows a close-up view of the head portion 13 of the endoscopic surgery apparatus 10. Arms 14a and 14b are shown in an open position. The arms 14a and 14b each extend longitudinally between a proximal end 32 and an opposing distal end 34. The arms 14a and 14b each define a concave inner surface 36 between the proximal end 32 and the distal end 34, and an outer surface 38 opposite the inner surface 36. The arms 14a and 14b each include a protruding member 40 extending from the concave inner surface 36. Each protruding member 40 extends between a proximal end surface 42 and an opposing distal end surface 44 thereof. The protruding members 40 of the arms 14a and 14b include respective guiding channel 16a and 16b, each of which aligns with a working channel passing through tubular member 11. Each guiding channel 16a, 16b extends through the respective protruding member 40, from the proximal end surface 42 to the distal end surface 44 thereof, such that the guiding channel 16a, 16b is enclosed by the respective protruding member 40. That is, each guiding channel 16a, 16b is in the form of a bore that extends through the respective protruding member 40, from the proximal end surface 42 to the distal end surface 44 thereof. Guiding channels 16a and 16b receive and guide surgical tools 25a and 25b, not shown in FIG. 2. The angle of arms 14a and 14b determines the angle that surgical tools 25a and 25b approach a surgical site. The surgeon may select an angle for the arms 14a and 14b such that the surgical tools 25a and 25b emerge parallel to each other, at an angle less than parallel, or at an angle more than parallel. The configuration of arms 14a and 14b will affect the degree to which the arms can be opened.

FIG. 2 also shows the distal terminals of channels 15a-d, wherein channel 15a is an optical channel, channel 15b is a third working channel, channels labeled 15c are illumination channels, and channel 15d is a fluid channel. In general, illumination channels 15c provide light to the surgical site so that the surgeon may view the site via the optical channel 15a. Fluid channel 15d may be used to deliver air, water, pharmaceutical fluids, or the like to the surgical site. Fluid channel 15d may also be used as a means for sensing the ambient pressure at the surgical site. Alternatively, pressure-sensing may be accomplished at other points on the head portion 13. The third working channel 15b may be advantageously employed as a means for evacuating fluids from the surgical site. In some embodiments, small particles of solid matter may also be evacuated by channel 15b.

The third working channel 15b does not pass through the guiding channels 16a and 16b in arms 14a and 14b. This gives the surgeon the ability to easily exert force in directions parallel to the axis of the tubular member 11. Thus, the surgeon is provided with the ability to exert force in many directions at the surgical site: forward or backward along the axis of the tubular member 11 or at various angles according to the angles of arms 14a and 14b.

Figure 3:
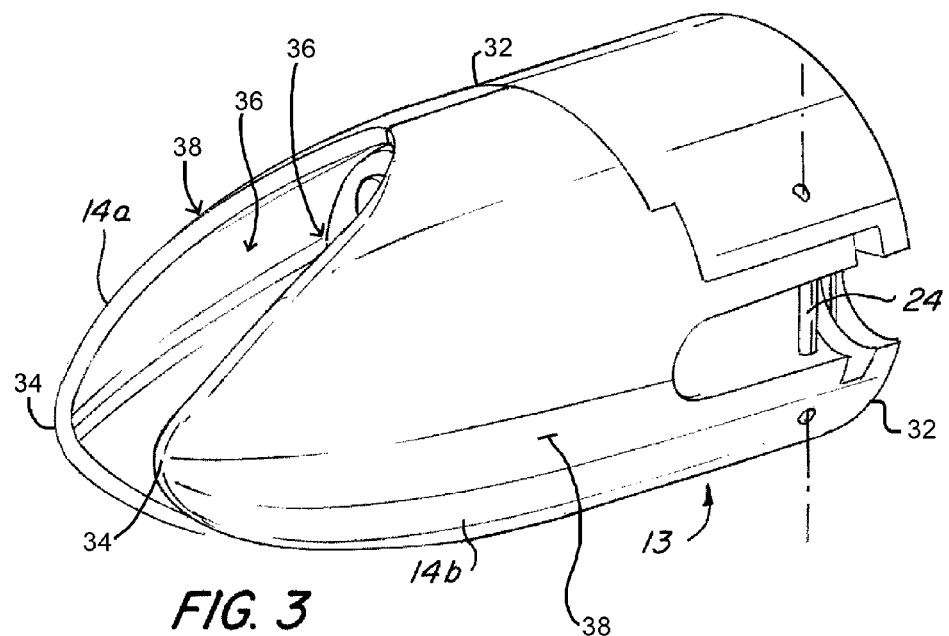
FIG. 3 is a perspective view of the distal end of the endoscopic surgery apparatus of FIG. 1, with arms in a closed position.

FIG. 3 shows head portion 13 of the endoscopic surgery apparatus 10 with arms 14a and 14b in a closed position. A hinge 24 is shown, which pivotably connects the proximal end 32 of arm 14b to the tubular member 11. The proximal end 32 of arm 14a is connected to tubular member 11 in the same fashion, however this connection is not shown in FIG. 3. In the closed position, arms 14a and 14b may provide a ramp for a surgical tool or instrument passing through working channel 15b. This ramp could be formed by the shape of the arms 14a and 14b or by the protruding members 40 formed on the inner surfaces 36 of the arms 14a and 14b. This ramp brings the tool or instrument directly into the field of view of optical channel 15a.

Figure 4:
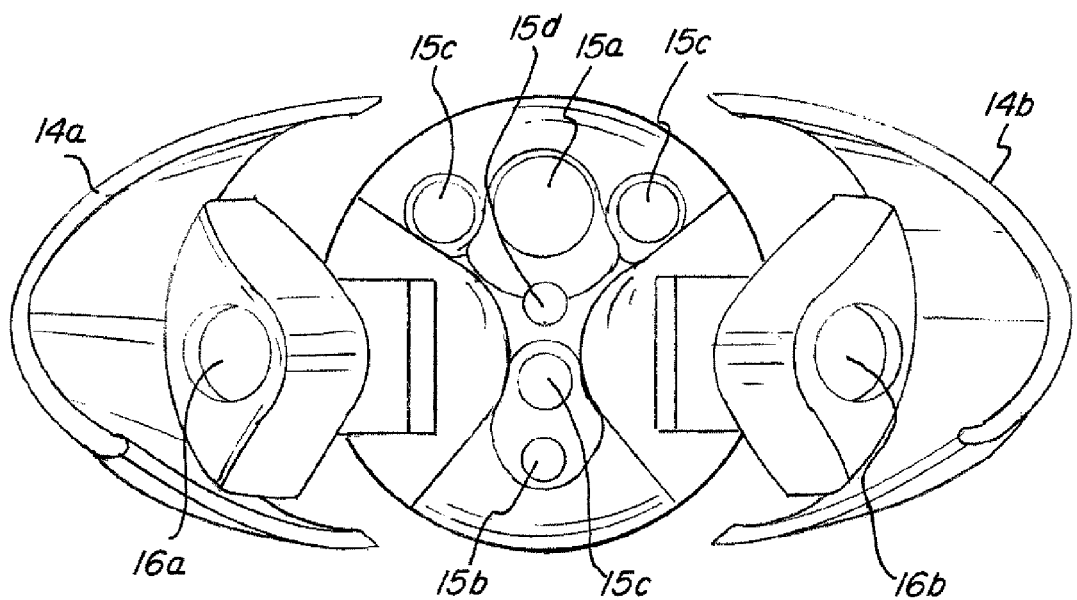
FIG. 4 is an end view of the distal end of the endoscopic surgery apparatus of FIG. 1, with arms in an open position.

FIG. 4 provides an alternative view of the head portion 13 of the endoscopic surgery apparatus 10 with arms 14a and 14b in an open position. Guiding channels 16a and 16b are shown in arms 14a and 14b. The distal terminals of various channels of the tubular member 11 are also shown. As before, there is an optical channel 15a, a working channel 15b, illumination channels 15c, and a fluid channel 15d.

Figure 5:
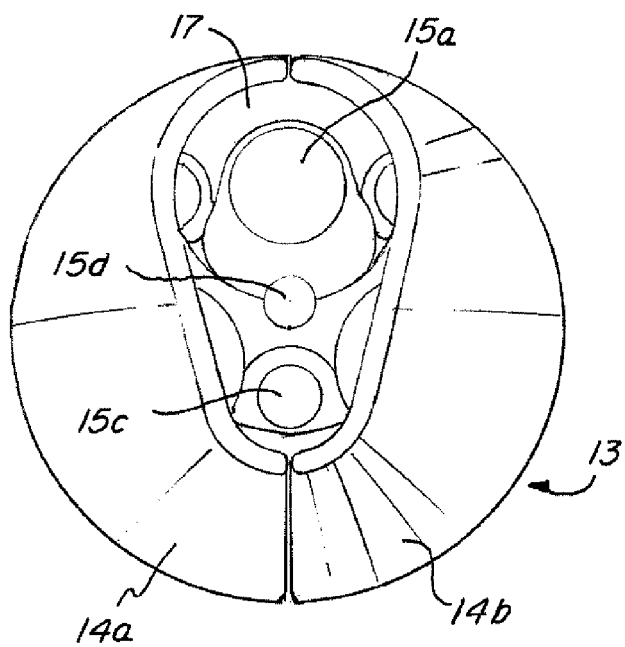
FIG. 5 is an end view of the distal end of the endoscopic surgery apparatus of FIG. 1, with arms in a closed position.

FIG. 5 shows an alternative view of the head portion 13 of the endoscopic surgery apparatus 10 with arms 14a and 14b in a closed position. This view shows one advantageous configuration of the apparatus 10, in which when the arms 14a and 14b are in a closed position, they define an opening 17. The opening 17 allows for utilization of the optical channel 15a, the fluid delivery channel 15d, and at least one of the illumination channels 15c in this embodiment even when the arms 14a and 14b are in a closed position. This allows a surgeon to more safely and effectively employ the endoscopic surgery apparatus 10, for example, during insertion of the apparatus into the body of a patient.

Figure 6:
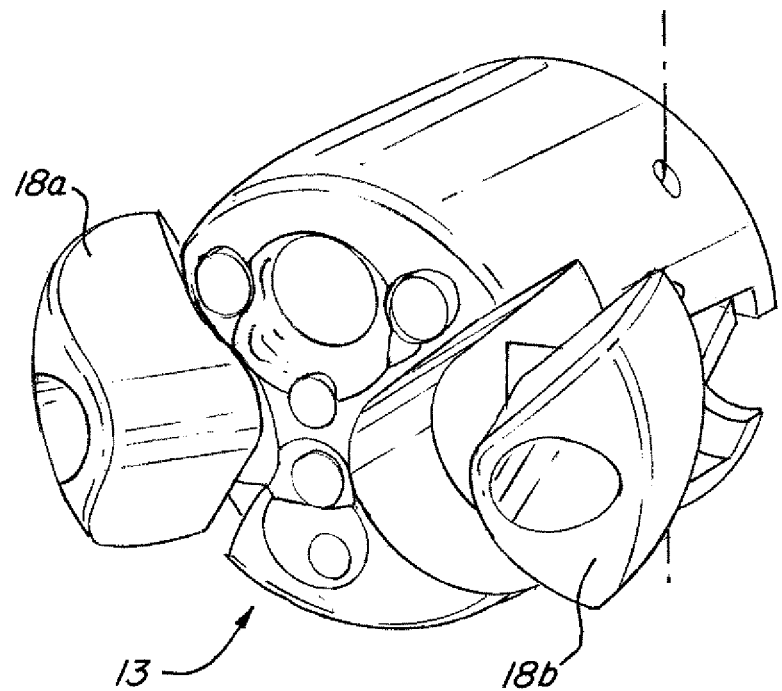
FIG. 6 is a perspective view of the distal end of the endoscopic surgery apparatus of FIG. 1 showing alternative arms in an open position.
Figure 7:
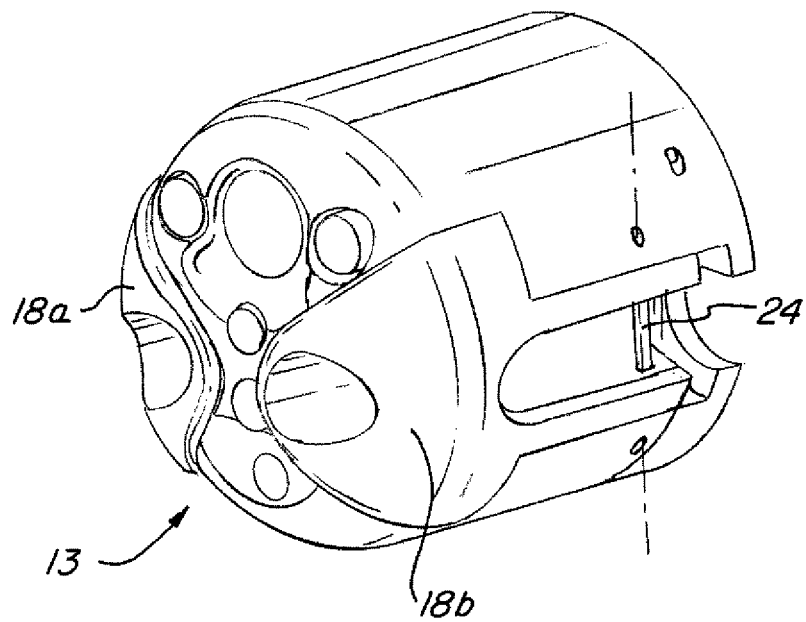
FIG. 7 is a perspective view of the distal end of the endoscopic surgery apparatus of FIG. 1 showing alternative arms in a closed position.

FIG. 6 shows head portion 13 utilizing arms 18a and 18b having a different configuration. The arms 18a and 18b are shown here in an open configuration and are shown in a closed position in FIG. 7. Hinge 24 is shown in FIG. 7, which pivotably connects arms 18a and 18b in a manner similar to the connection of arms 14a and 14b.

The present invention is advantageously employed using arms of various configurations, including, but not limited to, arms 18a and 18b and arms 14a and 14b. The various configurations of arms are interchangeable in the endoscopic surgery apparatus and one set of arms can be easily substituted for another set. Because of the wide variety of surgical applications possible with an endoscopic surgery apparatus according to the present invention, arms having different configurations are desirable for optimal performance of the system. The optimal arm configuration depends, for example, on such things as the organ on which surgery is to be performed, the type of surgery to be performed, or the condition of the patient.

For example, in some embodiments the arms 14a and 14b are constructed out of transparent material so that the optical channel 15a and the illumination channels 15c may be utilized even when the arms are in a closed position. In such a design, the opening 17 shown in FIG. 5 may not be necessary and the arms 14a and 14b could completely cover the head portion 13 of the endoscopic surgery apparatus 10. This could further ease insertion of the system into a patient. As a second example, in some embodiments the outer surface of the arms provides a further means for tissue manipulation at the surgical site. The outer surface could have members formed thereon for displacing tissue. In such a case, the arms are used to move tissue aside or obtain the desired degree of stretching of tissue. In a further example, the arms may also grasp tissue or organs to stabilize or remove them from the surgical site. Finally, some arm configurations may include a blade for snipping or cutting tissue. Certain arm configurations will perform these tasks better than other configurations. Thus, it is highly desirable to have the ability to interchange the arms located on the head portion 13 or even the entire head portion itself.

Most arm configurations that are advantageously employed in the present invention will have a shape such that when the arms are in a closed position, they act as an obturator. This obturator shape allows for easier insertion into the body because arms of this shape will harmlessly and temporarily displace tissue during insertion.

Figure 8:
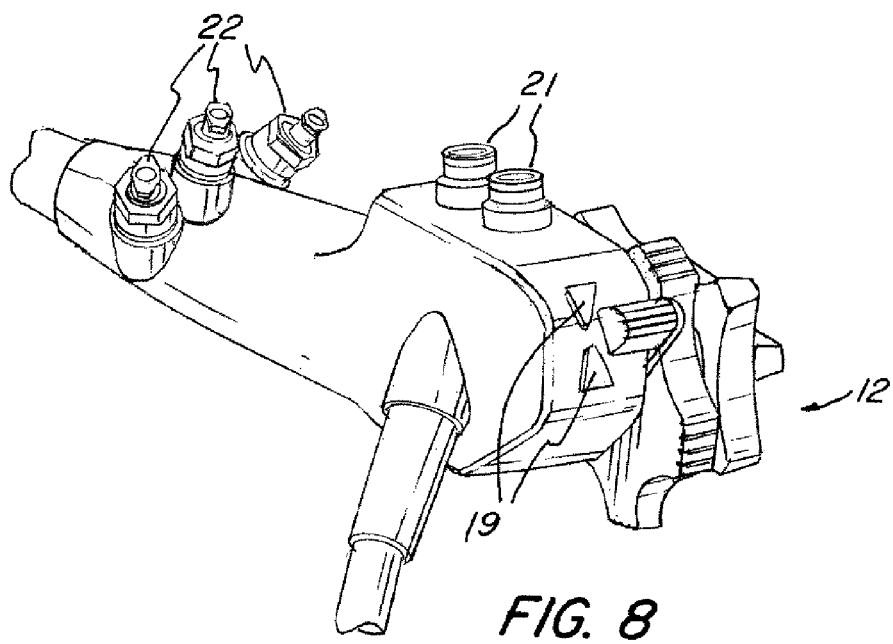
FIG. 8 is a perspective view of the handle on the proximal end of the endoscopic surgery apparatus of FIG. 1.
Figure 9:
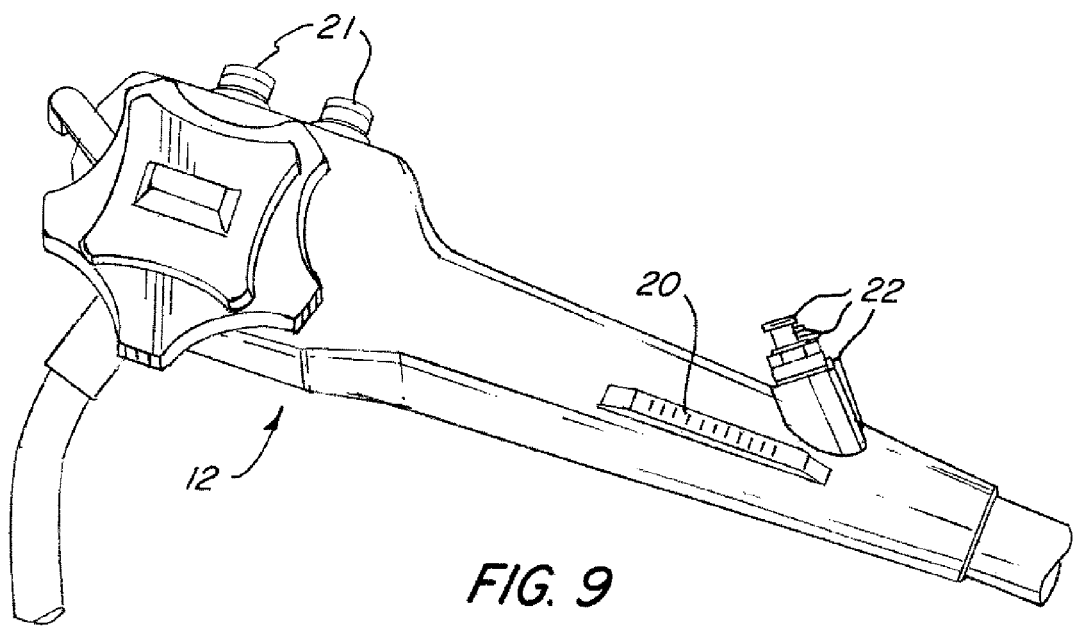
FIG. 9 is a second perspective view of the handle on the proximal end of the endoscopic surgery apparatus of FIG. 1.

FIGS. 8 and 9 show a close-up view of the handle 12 according to one embodiment of the invention. The handle 12 is attached at a proximal end of tubular member 11. The proximal terminals 22 of working channels 16a, 15b, and 16b as well as the proximal terminals 21 of the fluid channel 15d are shown. Camera controls 19 for controlling optical components utilizing the optical channel 15a are shown in FIG. 8. In some embodiments, the camera controls 19 control the degree of focus and zoom of the camera so that the surgeon is ensured a clear view of the surgical site. In some embodiments of the present invention, the system is advantageously adapted to permit video recording of the surgery for later analysis or educational purposes.

FIG. 9 also shows control switch 20 for controlling the position of the arms on the distal end. The control switch 20 may be of the sliding type as shown, a rotatable knob type, or any other appropriate design. In some embodiments, this switch advantageously has a locking mechanism so that the arms can be locked in a position selected by the surgeon.

Figure 10:
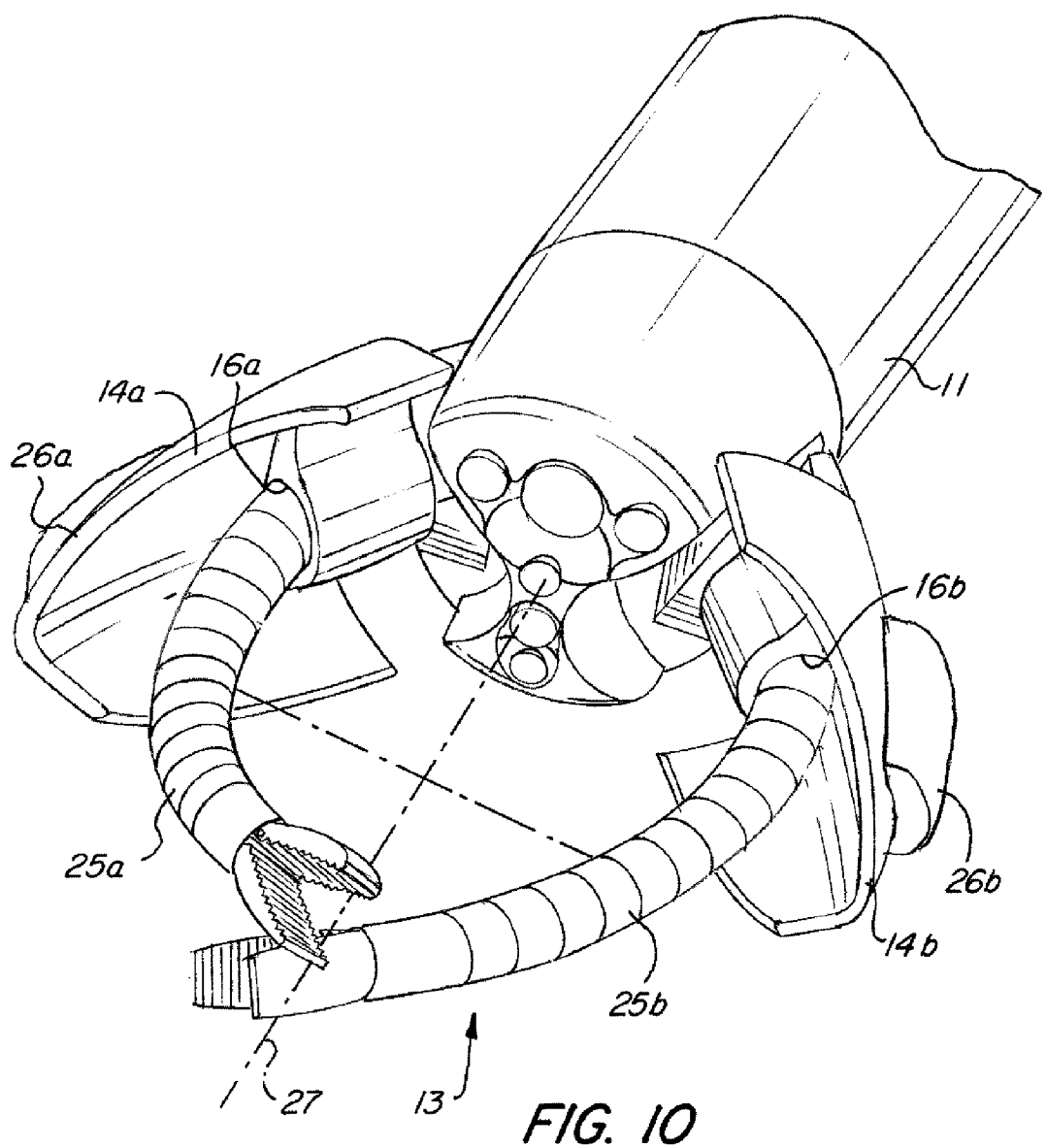
FIG. 10 is a perspective view of the distal end of the endoscopic surgery apparatus of FIG. 1 showing the arms in an open position and surgical tools protruding from the working channels therein.

Finally, FIG. 10 shows the head portion 13 of an endoscopic surgery apparatus 10 including surgical tools 25a and 25b. The arms 14a and 14b are in an open position and surgical tools 25a and 25b protrude from the guiding channels 16a and 16b. Due to the position of the arms 14a and 14b, the surgical tools 25a and 25b emerge parallel to the longitudinal axis 27 of the tubular member 11. In the embodiment shown in FIG. 10, arms 14a and 14b have tissue displacing members 26a and 26b formed on their outer surface for manipulating and displacing tissue. Thus, the angle of arms 14a and 14b determines the angle that surgical tools 25a and 25b approach a surgical site. Further, in some embodiments the head portion 13 of an endoscopic surgery apparatus 10, including the arms 14a and 14b is electrically isolated so as to enable electrosurgical procedures.

Thus, transgastric and transluminal surgical techniques can be improved by employing embodiments of the present invention. Implementation of an endoscopic surgery apparatus according to the present invention is simple. The following is an example of a method of employment of the embodiment presented in the description and figures. First, the surgeon inserts the endoscopic surgery apparatus 10 into the patient's stomach. The system enters the patient via the patient's mouth with the pivotable arms 14 in a closed position to minimize strain and trauma on the patient. In most cases, the surgeon guides the apparatus during insertion with a high degree of accuracy even when the arms 14 are in the closed position using the optical and illumination channels 15a, 15c, and 15e. This is possible either because of the advantageous opening 17 present between the pivotable arms 14 or because the arms 14 are constructed out of a transparent material. An incision is made in the stomach by passing a surgical tool 25 through working channel 15b. Once the incision is complete, with arms 14 still in the closed position, the head portion 13 is pushed through the incision into the peritoneal cavity.

Once the head portion 13 of the apparatus 10 reaches the intended surgical site, the surgeon moves the arms 14 from the closed position to the open position using the control 20. The angle of the opening of the arms 14 is chosen according to the desired angle of approach of the surgical tools. The position of the arms 14 can be locked using the locking feature of the control switch 20. Once the arms 14 are in an open position, the surgeon can deploy surgical tools for grabbing, cutting, or otherwise manipulating tissue from of the guiding channels 16a, 16b, and/or working channel 15b for performing the desired surgical tasks. The angle of arms 14 can be adjusted over the course of the surgery by means of the control switch 20.

Some embodiments of the present endoscopic surgery apparatus are adapted for robotic or electronic control. In these systems, highly precise and effective remote surgery is facilitated.

As shown in the drawings, in particular FIG. 10, the embodiment represented therein provides many of the important tools that a surgeon may need at a surgical site. The system creates a working triangle simply by opening the pivotable arms 14 and passing the surgical tools 23 through the guiding channels 16. The third working channel 15b allows the surgeon to exert force along the longitudinal axis of the apparatus 10. The system provides ample means for illumination and viewing of the surgical site, and also for the delivery of fluids such as air or water to the surgical site.

Therefore, the present invention provides an endoscopic surgical system, which may be used in transgastric or transluminal endoscopic surgery which minimizes the risk of infection, the recovery time, and the pain associated with the surgery, which has a thin profile so as to be easily insertable into a patient, which is capable of creating an effective working triangle for the surgeon, which allows easy illumination and viewing of a surgical site, and wherein fluid matter is easily delivered to a surgical site.

Although the invention has been described with reference to a particular arrangement of parts, features and the like, these are not intended to exhaust all possible arrangements or features, and indeed many other modifications and variations will be ascertainable to those of skill in the art.

What is claimed is:

1. An endoscopic surgery apparatus, comprising:
   a tubular member having a plurality of channels along its longitudinal axis, the tubular member having a proximal end and a distal end;
   a handle located on the proximal end of the tubular member; and
   at least two arms pivotably connected to the distal end of the tubular member, said at least two arms each having a protruding member extending from an inner surface of the respective arm, the protruding member extending between a proximal end surface and an opposing distal end surface thereof, and a guiding channel passing through each protruding member, from the proximal end surface to the distal end surface thereof, such that the guiding channel is enclosed by the respective protruding member, wherein each guiding channel is adapted to receive an endoscopic surgical tool therethrough,
   an optical device, at least a portion of which is located at the distal end of the tubular member,
   wherein said at least two arms, when in a closed position, cover at least a portion of the distal end of the tubular member and form an obturator shape,
   wherein the at least two arms are shaped so that, when in the closed position, an opening is defined between the arms, the opening configured to permit viewing of a surgical site therethrough via at least the portion of the optical device located at the distal end of the tubular member.

2. The endoscopic surgery apparatus of claim 1, wherein said tubular member comprises, in order from its proximal end, a shaft portion coupled to said handle, a series of vertebrae coupled to the shaft portion, and a head member coupled to the most distal vertebra of the series of vertebrae, wherein the head member is the distal end to which the arms are pivotably connected.

3. The endoscopic surgery apparatus of claim 1, wherein said at least two arms are pivotable between a closed position and an open position.

4. The endoscopic surgery apparatus of claim 3, wherein a mechanism on said handle permits locking the at least two arms in any selected position.

5. The endoscopic surgery apparatus of claim 3, wherein the at least two arms are adapted to grasp tissue at a surgical site when the at least two arms are pivoted.

6. The endoscopic surgery apparatus of claim 1, wherein said at least two arms are detachably connected to the distal end of the tubular member and are interchangeable with arms of different configurations.

7. The endoscopic surgery apparatus of claim 1, wherein the optical device includes an optical channel in said tubular member for the transmission of images, and at least one other of said channels in said tubular member is an illumination channel for the transmission of light.

8. The endoscopic surgery apparatus of claim 7, wherein the opening is further configured to permit illumination of the surgical site therethrough via the at least one illumination channel.

9. The endoscopic surgery apparatus of claim 1, wherein said plurality of channels includes at least one working channel adapted to receive an endoscopic surgical tool.

10. The endoscopic surgery apparatus of claim 9, wherein at least one protruding member is configured to deflect an endoscopic surgical tool running through said working channel.

11. The endoscopic surgery apparatus of claim 1, wherein each one of the at least two arms is connected to the distal end of the tubular member such that each one of the at least two arms pivots about only a single hinge.

12. The endoscopic surgery apparatus of claim 1, wherein each of the at least two arms includes at least one tissue displacing member on an outer surface thereof, the at least one tissue displacing member adapted to displace tissue when the arm on which the tissue displacing member is disposed is pivoted.

13. The endoscopic surgery apparatus of claim 12, wherein the at least one tissue displacing member protrudes in a direction oblique to the longitudinal axis of the tubular member.

14. The endoscopic surgery apparatus of claim 13, wherein the tissue displacing members are rounded protrusions.

15. The endoscopic surgery apparatus of claim 1, wherein a first channel of the plurality of channels is aligned with a guiding channel of a first arm of the at least two arms for insertion of a first endoscopic surgical tool, and a second channel of the plurality of channels is aligned with a guiding channel of a second arm of the at least two arms for insertion of a second endoscopic surgical tool.

16. An endoscopic surgery apparatus, comprising:
a tubular member having a plurality of channels along its longitudinal axis, the tubular member having a proximal end and a distal end;
a handle located on the proximal end of the tubular member; and
at least two arms pivotably connected to the distal end of the tubular member, said at least two arms each having a protruding member extending from an inner surface of the respective arm, the protruding member extending between a proximal end surface and an opposing distal end surface thereof, and a guiding channel passing through each protruding member, from the proximal end surface to the distal end surface thereof, such that the guiding channel is enclosed by the respective protruding member, wherein each guiding channel is adapted to receive an endoscopic surgical tool therethrough,
wherein said at least two arms, when in a closed position, cover at least a portion of the distal end of the tubular member and form an obturator shape,
wherein at least a portion of each of said at least two arms is transparent.

17. The endoscopic surgery apparatus of claim 16, wherein an entirety of each of said at least two arms is transparent.

18. The endoscopic surgery apparatus of claim 16, further comprising an optical device, at least a portion of said optical device located at the distal end of the tubular member, wherein a surgical site is viewable through the transparent portions of said at least two arms using at least the portion of the optical device located at the distal end of the tubular member.

* * * * *